(12) United States Patent
Moss et al.

(10) Patent No.: US 12,139,460 B2
(45) Date of Patent: *Nov. 12, 2024

(54) LIQUID-LIQUID EXTRACTION OF PURIFIED PSYCHOACTIVE ALKALOID

(71) Applicant: PSILO SCIENTIFIC LTD, Vancouver (CA)

(72) Inventors: Ryan Moss, Vancouver (CA); Benjamin Lightburn, Vancouver (CA); Lisa Ranken, Lake Country (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/683,505

(22) PCT Filed: Oct. 6, 2022

(86) PCT No.: PCT/CA2022/051482
§ 371 (c)(1),
(2) Date: Feb. 13, 2024

(87) PCT Pub. No.: WO2023/056561
PCT Pub. Date: Apr. 13, 2023

(65) Prior Publication Data
US 2024/0327348 A1    Oct. 3, 2024

(30) Foreign Application Priority Data
Oct. 7, 2021   (CA) ................. CA 3133547

(51) Int. Cl.
*A61K 36/00* (2006.01)
*B01D 11/02* (2006.01)
*B01D 11/04* (2006.01)
*C07D 209/16* (2006.01)

(52) U.S. Cl.
CPC ........ *C07D 209/16* (2013.01); *B01D 11/0257* (2013.01); *B01D 11/0288* (2013.01); *B01D 11/0457* (2013.01); *B01D 11/0492* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 3,183,172 A | 5/1965 | Heim et al. | |
| 11,331,357 B2 * | 5/2022 | Lightburn | A61K 31/48 |
| 2020/0375967 A1 | 12/2020 | Stamets | |
| 2020/0385378 A1 | 12/2020 | Tewari | |

FOREIGN PATENT DOCUMENTS

| CA | 3088384 | 10/2020 |
|---|---|---|
| CA | 3169783 | 9/2021 |

OTHER PUBLICATIONS

Wasser, Brennendes, "Extraction of Bufotenine (5-OH-DMT) from Anadenanthera colubrina"; DMT Nexus Forum, Oct. 3, 2020 https://www.dmt-nexus.me/forum/default.aspx?g=posts&t=93378.

Ott, J., "Pharmañopo—Psychonautics: Human Intranasal, Sublingual, Intrarectal, Pulmonary and Oral Pharmacology of Bufotenine"; Journal of Psychoactive Drugs, 33(3), pp. 273-281. Jul.-Sep. 2001(Jul.-Sep. 2001) [ISSN:2159-9777] https://www.tandfonline.com/doi/abs/10.1080/02791072.2001.10400574.

Moreira et al, "Concise Synthesis of N,N-Dimethyltryptamine and 5-Methoxy-N,N-dimethyltryptamine Starting with Bufotenine from Brazilian *Anadenanthera* ssp", Natural product communications, 10(4), pp. 581-584. Apr. 1, 2015 [ISSN: 1934-578x] https://journals.sagepub.com/doi/abs/10.1177/1934578X1501000411.

Wieczorek et al, "Bioactive Alkaloids of Hallucinogenic Mushrooms", Chapter 5 in Studies in Natural Products Chemistry, 46, pp. 153-181. Dec. 2015 [ISSN: 978-0-444-63462-7] [ISSN: 1572-5995] https://dx.doi.org/10.1016/B978-0-444-63462-7.00005-1.

Takeo et al., "The significance of methyl groups in the electroencephalographic effects of indolealkylamines in the rabbit", Biochemical Pharmacology, 16(6), Jun. 1967, pp. 1013-1022. [ISSN: 0006-2925] https://doi.org/10.1016/0006-2952(67)90274-2.

Dyer et al., "Vasoconstriction Produced by Hallucinogens on Isolated Human and Sheep Umbilical Vasculature", Journal Pharmacology and Experimental Therapeutics, 184(2), Feb. 1, 1973, pp. 366-375. [ISSN: 0022-3565] https://jpet.aspetjournals.org/content/184/2/366.

Casale, J., "An Aqueous-Organic Extraction Method for the Isolation and Identification of Psilocin from Hallucinogenic Mushrooms", Journal of Forensic Sciences, 30(1), pp. 247-250. Jan. 1, 1985 [DOI: 10.1520/JFS10989J].

Gartz, H. J., "Extraction and analysis of indole derivatives from fungal biomass", Journal of Basic microbiology, 34(1), pp. 17-22. Jan. 1, 1994, https://doi.org/10.1002/jobm.3620340104.

(Continued)

*Primary Examiner* — Russell G Fiebig
(74) *Attorney, Agent, or Firm* — Damien G Loveland; Valuetech Patent Agency Inc.

(57) ABSTRACT

A solution of extracted psychoactive alkaloids is obtained from psychoactive organisms or an existing extract using a neutral or acidic solvent. Acid extraction of psychoactive compounds from psychoactive organisms results in the dephosphorylated form of psychoactive alkaloids. The solution is basified to deprotonate the alkaloids. It is then subjected to a liquid-liquid extraction with a water-immiscible solvent. The resulting psychoactive organic layer is then subjected to a second liquid-liquid extraction with weakly acidic water. The resulting psychoactive aqueous layer is then dried to form a powder with the psychoactive alkaloid in a conjugate salt form. The powder may be standardized to a desired concentration of psychoactive alkaloid by the addition of an excipient. Alternatively, the standardization may be carried out on the psychoactive aqueous phase. Obtaining the psychoactive alkaloid in the conjugate salt form reduces the amount of non-psychoactive components included in the final extract.

20 Claims, 2 Drawing Sheets

(56) References Cited

OTHER PUBLICATIONS

Chadeayne et al., "The fumarate salts of the N-isopropyl-N-methyl derivatives of DMT and psilocin", Acta Crystallographica Section E: Crystallographic Communications, 75(9), pp. 1316-1320. Aug. 16, 2019, https://doi.org/10.1107/S2056989019011253.

Pham et al., "Psilacetin derivatives: fumarate salts of the methyl-ethyl, methyl-allyl and diallyl variants of the psilocin prodrug", Acta Crystallographica Section E: Crystallographic Communications, 77(2), pp. 101-106. Jan. 8, 2021, https://doi.org/10.1107/S2056989021000116.

Chadeayne et al., "Norpsilocin: freebase and fumarate salt", Acta Crystallographica Section E: Crystallographic Communications, 76(4), pp. 589-593. Mar. 27, 2020, https://doi.org/10.1107/S2056989020004077.

Atlabachew, M. et al., "Preparative HPLC for large scale isolation, and salting-out assisted liquid-liquid extraction based method for HPLC-DAD determination of khat (Catha edulis Forsk) alkaloids", Chemistry Central Journal, 11(1), pp. 1-10. Oct. 2017 https://doi.org/10.1186/s13065-017-0337-6.

Vaupel D B et al., "The inhibition of food intake in the dog by LSD, Mescaline, psilocin, d-amphetamine and phenylisopropylamine derivatives", Life Science, vol. 24, No. 26, pp. 2427-2431, Jun. 25, 1979.

Migliaccio et al., "Comparison of Solution Conformational Preferences for the Hallucinogens Bufotenin and Psilocin Using 360-MHz Proton NMR Spectroscopy", Journal of Medicinal Chemistry, vol. 24, No. 2, pp. 206-209, Jan. 2, 1981.

Aghajanian et al., "Hallucinogenic Indoleamines: Preferential Action Upon Presynaptic Serotonin Receptors", Psychopharmacology Communications, vol. 1, No. 6, pp. 619-629, Jan. 1, 1976.

Stromberg, "The Isolation of Bufotenine from Piptadenia Peregrina", p. 1707, Mar. 20, 1954.

\* cited by examiner

LIQUID-LIQUID EXTRACTION OF PURIFIED PSYCHOACTIVE ALKALOID

TECHNICAL FIELD

This application relates to the extraction of active ingredients from psychoactive alkaloid sources. More specifically, it relates to extracting and purifying psychoactive compounds from psychedelic organisms or lower-purity psychoactive extracts using liquid-liquid extractions.

BACKGROUND

A psychoactive substance is a chemical substance that changes brain function and results in alterations in perception, mood, consciousness, cognition, or behavior. The psychoactivity of these substances may include sedative, stimulant, euphoric, deliriant, and hallucinogenic effects. These substances have been used recreationally, to purposefully improve performance or alter one's consciousness, and as entheogens for ritual, spiritual, or shamanic purposes. Some categories of psychoactive compounds have also shown therapeutic values and are prescribed by physicians and other healthcare practitioners. Varieties of mushrooms have played important roles in some societies. The active ingredients in psychedelic mushrooms, especially psilocybin mushrooms with psychoactive compounds such as psilocybin, psilocin, baeocystin, norbaeocystin, ibotenic acid, and norpsilocin, have been found to have medicinal properties including relief of symptoms of various diseases and conditions.

The active constituents of the majority of psychoactive plants, fungi, animals, or yeasts fall within a class of basic, naturally occurring, nitrogen-containing, organic compounds called alkaloids (e.g. nicotine, morphine, cocaine, mescaline, caffeine, ephedrine, psilocin). Alkaloids have a wide range of pharmacological activities including antimalarial, antiasthma, anticancer, cholinomimetic, vasodilatory, antiarrhythmic, analgesic, antibacterial, and antihyperglycemic activities. Many alkaloids have found use in traditional or modern medicine, or as starting points for drug discovery. Recently, psychotropic and stimulant activities of psychoactive alkaloids have been gaining interest from researchers as therapeutic agents for treating various conditions such as alcoholism, opioid addiction and pain to name a few.

Psychoactive alkaloids present in natural sources can be broadly divided into two categories, which are phosphorylated psychoactive alkaloids and dephosphorylated psychoactive alkaloids, although other non-phosphorylatable psychoactive alkaloids may also be present.

Phosphorylated psychoactive alkaloids are phosphoric acid esters of dephosphorylated psychoactive alkaloids. For example psilocybin is a phosphoric acid ester of psilocin, at the 4th position. Phosphorylated psychoactive alkaloids are biosynthesized in natural sources. Dephosphorylated psychoactive alkaloids are the bioactive forms that are converted from phosphorylated alkaloids, through phosphatase action or chemical hydrolysis, and released when the natural source is damaged, harvested, or eaten. Because of this phenomenon, phosphorylated psychoactive alkaloids are often either partially or entirely converted to dephosphorylated psychoactive alkaloids during the alkaloid extraction process, which involves harvesting as a necessary prior step.

Although the dephosphorylated psychoactive alkaloids are the bioactive form of their counterpart phosphorylated psychoactive alkaloids, dephosphorylated psychoactive alkaloids are easily degraded into non-bioactive compounds in the presence of light, heat, and oxygen. For example, oxidation of psilocin begins rapidly when exposed to air, especially in solution, and heat increases the oxidation rate. From our own data, the oxidation of psilocin in a moist and/or high light environment begins immediately. For example, this leads to about 10% decay within 30 minutes, 25% after 5 hours, and 40-60% at 20 hours when shielded from light. Due to this instability of the dephosphorylated psychoactive alkaloids, the bioactivity of the psychoactive alkaloid extracts may also be unstable over time.

The concentration of active psilocybin mushroom compounds varies not only from species to species, but also from mushroom to mushroom within a given species, subspecies or variety. The same holds true even for different parts of the same mushroom or mycelium. Various methods of extraction, which have been used to separate natural extracts from a variety of mushrooms, have resulted in difficulties with large crop-to-crop variability. This is also true for plants. Different solvent choices extract the psychoactive compounds equally, some of them selectively extract one or the other, and some convert the compounds between each other or degrade them into non-psychoactive compounds. Many extraction processes for extracting standardized concentrations of the compounds for direct medical use are usually complex. This results in expensive extraction processes and a high cost of isolated, natural extracts.

U.S. Pat. No. 3,183,172 to Heim et al. relates to an industrial process for the isolation of active compounds from mushrooms grown under predetermined conditions. With the predetermined growing conditions, mushrooms grow with ten times more active mycelium and *sclerotium*, and increased concentrations of psychoactive compounds. However, a large portion of the target compounds are lost during the extraction process or not extracted at all. This problem is significant with respect to very potent extracts of psilocybin mushrooms, considering that a normal dose for use ranges from only 5 mg to 25 mg. The extracted psychoactive compounds are generally without a stable and standardized concentration. Other extraction processes may use time consuming and degradation-inducing steps, such as defatting the raw material or isolating the neutral psychoactive alkaloid itself.

To date, the focus has largely been on synthetic preparations of these compounds because of the many difficulties associated with naturally extracted preparations. It is currently infeasible and expensive to extract psilocybin from mushrooms, and even the best chemical synthesis methods require expensive and difficult-to-source starting substrates. However, extracts or compositions with an active ingredient made from natural sources generally have increased consumer acceptance and a lower cost of production compared to synthetic compositions. There may be potential benefits of multiple natural compounds working synergistically, colloquially known as the "entourage" or "halo" effect. However, the availability of psychoactive alkaloid compositions with a desired specific psychoactive alkaloid content is a major challenge faced by researchers. It is even more challenging to produce consistent formulations when the concentration of active ingredients being extracted is typically very low in the natural source. Maintaining physical and chemical stability is also an issue with these compositions. Extracts or compositions containing psychoactive alkaloids are often not amenable to drying, processing (due to poor flowability), or packaging methods such as tabulation or encapsulation.

Accordingly, there is a need of improved methods for extracting and producing standardized preparations of the target compounds for medical use while using acceptable solvent systems to create a more consistent supply chain.

This background information is provided to reveal information believed by the applicant to be of possible relevance to the present invention. No admission is necessarily intended, nor should be construed, that any of the preceding information constitutes prior art against the present invention.

SUMMARY OF INVENTION

The present disclosure is directed to the extraction of psychoactive compounds from psychedelic organisms, for example from the Psilocybe cubensis species of psychedelic mushroom. The extraction may be an acid extraction in order to promote dephosphorylation. The filtrate from the extraction, whether the solvent was neutral or acidic, is then adjusted to an alkaline pH in order to convert the dephosphorylated alkaloid from the cationic form to the deprotonated form. For purification, the filtrate then undergoes a first liquid-liquid extraction to an organic layer, followed by a second liquid-liquid extraction to an aqueous layer, which is then dried to result in the extract. The extract may then be standardized and formulated.

Steps such as defatting the raw material or isolating the neutral psychoactive alkaloid itself are not required in the disclosed process, which proceeds directly towards formation of a conjugate salt of the psychoactive alkaloid. The extract with the conjugate salt has an increased oxidative stability compared to the deprotonated, isoelectric or neutral forms of the psychoactive alkaloids. The extract is also water-soluble, which is therefore well-suited to oral administration, whether formulated into a capsule, tablet, gel, liquid tincture, beverage, or nasal spray. Since the disclosed process selectively extracts the alkaloids themselves, other unnecessary or undesirable components are left behind in the process. As such, the process allows for the use of a larger range of raw material grades to be used in production of the finished extract. The selective extraction also provides the opportunity for high active ingredient concentrations in the final extract, which can therefore be considered to be a refined, natural product.

Disclosed is a process for extracting psychoactive alkaloid from a psychoactive alkaloid source comprising the steps of: obtaining a psychoactive filtrate from the psychoactive alkaloid source using a solvent consisting of (a) one or more members selected from the group consisting of C1-C4 aliphatic alcohols, C3-C4 ketones and water, or (b) an acid and one or more members selected from said group; basifying the psychoactive filtrate to result in a basified psychoactive filtrate; performing a first liquid-liquid extraction on the basified psychoactive filtrate using a water-immiscible solvent to yield a psychoactive organic layer, wherein the water-immiscible solvent is immiscible with the basified psychoactive filtrate; performing a second liquid-liquid extraction on the psychoactive organic layer using weakly-acidified water to yield a psychoactive aqueous layer, wherein the weakly-acidified water has a concentration in a range of 0.001-0.5 N; and removing water from the psychoactive aqueous layer to yield a dry, psychoactive extract comprising the psychoactive alkaloid.

Also disclosed is a composition comprising an extract comprising a conjugate salt of a psychoactive alkaloid and an excipient.

Further disclosed is a psychoactive alkaloid extract made by: obtaining a psychoactive filtrate from a psychoactive alkaloid source using a solvent consisting of one or more members selected from the group consisting of C1-C4 aliphatic alcohols, C3-C4 ketones and water; basifying the psychoactive filtrate; performing a first liquid-liquid extraction on the basified psychoactive filtrate using a water-immiscible solvent to yield a psychoactive organic layer; performing a second liquid-liquid extraction on the psychoactive organic layer using weakly-acidified water to yield a psychoactive aqueous layer, wherein the weakly-acidified water has a concentration in a range of 0.001-0.5 N; and removing water from the psychoactive aqueous layer to yield a dry, psychoactive extract comprising the psychoactive alkaloid.

Still further disclosed is a dephosphorylated psychoactive alkaloid extract made by: soaking a biomass of one or more dried, ground, raw psychedelic organisms in a solvent consisting of an acid and one or more members selected from the group consisting of C1-C4 aliphatic alcohols, C3-C4 ketones and water to result in the psychoactive alkaloid in its dephosphorylated form being dissolved in the solvent; filtering an undissolved portion of the biomass from the solvent to result in a psychoactive filtrate; adding a base to the psychoactive filtrate to obtain a basified psychoactive filtrate; performing a first liquid-liquid extraction on the basified psychoactive filtrate using a water-immiscible solvent to yield a psychoactive organic layer; performing a second liquid-liquid extraction on the psychoactive organic layer using weakly-acidified water to yield a psychoactive aqueous layer, wherein the weakly-acidified water has a concentration in a range of 0.001-0.5 N; and removing water from the psychoactive aqueous layer.

This summary does not necessarily describe all the features of the invention. It provides a simplified, non-exhaustive introduction to some aspects of the invention, without delineating the scope of the invention.

BRIEF DESCRIPTION OF DRAWINGS

The following drawings illustrate embodiments of the invention, which should not be construed as restricting the scope of the invention in any way.

DESCRIPTION

A. Glossary

Figure 1:
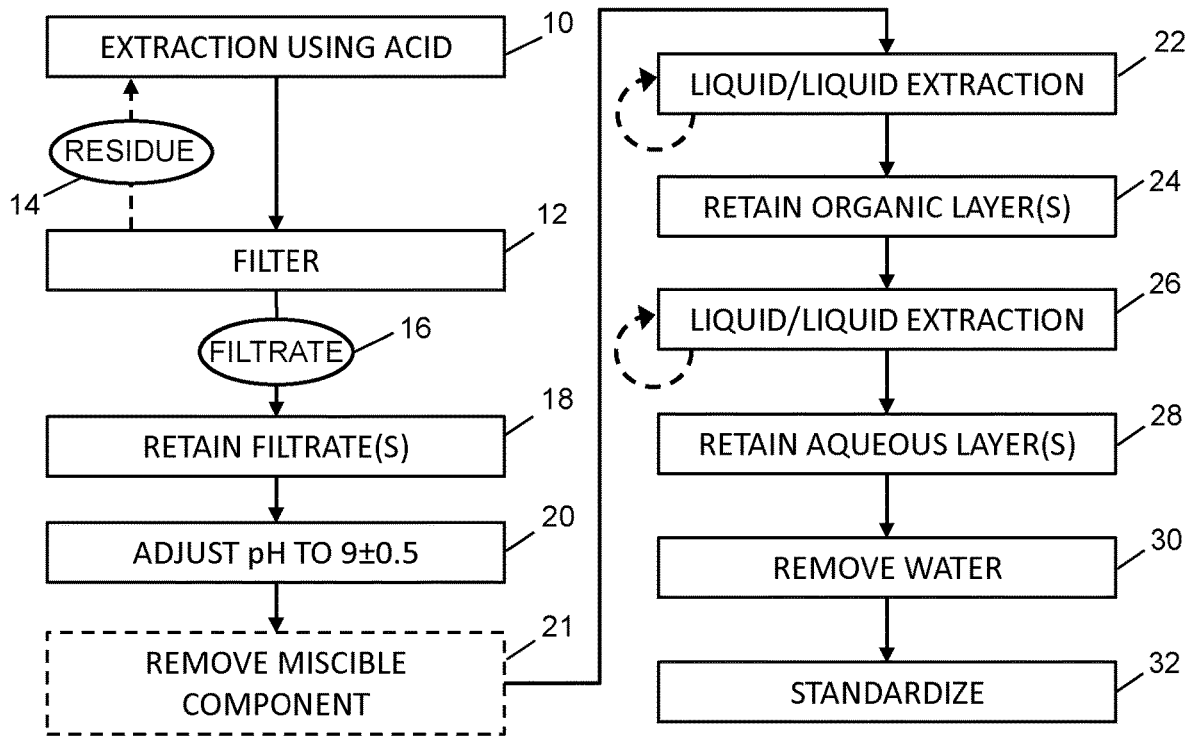
FIG. 1 is a flowchart showing a process for extracting psychoactive alkaloids from psychedelic organisms, according to an embodiment of the present invention.

Psychoactive alkaloid source—as used herein refers to a psychedelic organism, a group of psychedelic organisms, or parts of psychedelic organisms. A psychoactive alkaloid source may also be a pre-existing extract or a solution with a phosphorylated psychoactive alkaloid, a dephosphorylated psychoactive alkaloid, or a combination of both a phosphorylated psychoactive alkaloid and a dephosphorylated psychoactive alkaloid.

Psychedelic organism—this refers to any lifeform that naturally produces a psychoactive alkaloid. A psychedelic organism may be, for example, a fungus, a mycelium, a spore, a plant, a tree, an animal, a protist, a yeast or a bacterium. The organism may be, for example, *Anadenanthera colubrina, Anadenanthera peregrina* or *Incilius alvarius*.

Psychedelic fungi, psilocybin fungi, or psilocybin mushrooms—these are a group of fungi that include at least one psychoactive alkaloid, and often include psilocybin and psilocin. They may also include other psychoactive alkaloids such as baeocystin, norbaeocystin, ibotenic acid and norpsilocin. The genera of these mushrooms include *Copelandia, Gymnopilus, Inocybe, Panaeolus, Pholiotina, Pluteus, Amanita* and *Psilocybe*.

*Psilocybe* mushrooms—these form a genus of gilled mushrooms in the family Hymenogastraceae. Most species contain the psychoactive alkaloids psilocybin, psilocin and baeocystin.

Psilocybin—this is an example of a psychoactive alkaloid and is a psychedelic prodrug produced by numerous species of mushrooms, collectively known as psilocybin mushrooms. Psilocybin is converted by the body to psilocin, which has mind-altering effects such as euphoria and hallucinations, but can also lead to nausea and panic attacks.

Psychoactive alkaloid—this refers alkaloids that upon ingestion are capable of changing brain function, resulting in alterations in perception, mood, consciousness, cognition, or behavior, for example. Psychoactive alkaloids are abundant in nature and can be obtained from psychedelic organism sources such as a fungus, an animal, a mycelium, a spore, a plant, a bacterium, or a yeast. Examples of psychoactive alkaloids include, but are not limited to, psilocybin, psilocin, baeocystin, norbaeocystin, norpsilocin, aeruginascin, bufotenin, bufotenidine, 5-MeO-DMT (5-methoxy-N,N-dimethyltryptamine), N,N-dimethyltryptamine (DMT), ergine (LSA), ergonovine, ergometrine, ibotenic acid, muscimol, lysergic acid hydroxyethylamide (LSH), elymoclavine, ergometrinine, and/or chanoclavine.

Phosphorylatable psychoactive alkaloid—refers to psychoactive alkaloids that have phosphorylated derivatives, and includes psychoactive alkaloids in both their phosphorylated and dephosphorylated forms.

Deprotonated form—refers to the freebase form of an alkaloid, or equivalently its conjugate base form. For example, it refers to the psilocin itself, unconjugated, rather than psilocin HCL, psilocin fumarate, psilocin citrate, psilocin acetate etc.

Isoelectric form or neutral form—refers to a molecule having an average neutral charge taking into consideration its environment, particularly the pH of its environment, for example, it refers to the non-acidic form of a psychoactive alkaloid.

Conjugate salt—herein refers to the salt formed when a conjugate acid or a conjugate base are combined with the ionic (non-neutral) form of a compound (in this case an alkaloid) and dried. For example, psilocin HCL, psilocin citrate, psilocin fumarate, psilocin acetate.

Weak acid—refers to an acid that is not completely dissociated when added to water.

Strong acid—refers to an acid that is completely dissociated when added to water.

Weakly-acidified water—refers to a dilute mixture of a strong acid or a weak acid in water. The pH will depend on the concentration of the weak or strong acid in the water. In the present disclosure, the concentration may be in the range of 0.001-0.5 N and in some embodiments corresponds to the molar content of the alkaloid in the organic layer, as each molecule of acid can deprotonate and conjugate with 1-4 molecules of alkaloid.

Excipient—an excipient is any component or group of components added to an active ingredient to make a composition. An excipient is inert in relation to the active ingredient, in that it essentially does not act in the same way as the active ingredient. An excipient may be completely inert, or it may have some other property that protects the integrity of the active ingredient or assists its uptake into the human body. There are multiple types of excipient, each having a different purpose, and a given excipient may fulfill more than one purpose. Examples of types of excipient include flowability agents, flavorants, colorants, palatants, antioxidants, bioavailability-increasing agents, viscosity modifying agents, tonicity agents, drug carriers, sustained-release agents, comfort-enhancing agents, emulsifiers, solubilizing aids, lubricants, binding agents and stabilizing agents. The excipients used in the present invention are acceptable for use in pharmaceutical or nutraceutical applications or as food ingredients. Specific excipients include pectin, rice husks, rice, xanthum gum, gum arabic, beta cyclodextrin, alpha cyclodextrin, microcrystalline cellulose, sorbitol, dextrose, guar gum, acacia gum, cellulose gum, talc, magnesium stearate, silicon dioxide, ascorbic acid, maltodextrin, sodium benzoate, sodium phosphate and sodium citrate.

Carrier—means an excipient that aids in delivery of the active ingredient or provides bulk to the composition. The amount of carrier included in a composition can vary widely in order to control the concentration of the active ingredient in the composition. Examples of carriers are starch, maltodextrin, tapioca maltodextrin or rice maltodextrin, alpha and beta cyclodextrin, microcrystalline cellulose (MCC), gum arabic, xanthum gum, guar gum and cellulose gum.

B. Process Starting from Biomass

Referring to FIG. 1, a flowchart is shown of the basic steps of the extraction process for extracting and dephosphorylating psychoactive compounds from psychedelic organisms. The dephosphorylation aspect of the present invention relates to psychoactive alkaloids that have phosphorylated forms, and not to other psychoactive alkaloids that may be present in a psychoactive alkaloid source. The strain or harvest should be selected with some care, as there may be no or substantially no phosphorylatable psychoactive alkaloids in the psychoactive alkaloid source, or they may represent as much as 80-90% of the total alkaloid content, for example.

In step 10, an acidic solvent is added to a biomass of one or more dried and ground, raw organisms, such that the solvent comes into contact with the biomass in order to extract the psychedelic alkaloids from it. In some embodiments, the raw organism includes, for example, *Psilocybe cubensis* mushrooms, *Psilocybe* cyanescens mushrooms, *Amanita muscaria* mushrooms or a mixture of any of these. Other species of psychedelic mushrooms or psychedelic organisms may also be used.

For the extraction of psychoactive compounds from mushrooms, the parts of the mushrooms, if used, include, for example, caps, gills, stems, and hyphae, and more particularly, any part of the psilocybin mushroom or mycelium can be included. In other cases, the raw psilocybin fungus parts used include only caps, or only stems, or only gills, or only hyphae or only mycelium or any mixture thereof. In still other cases, parts of the raw psilocybin fungus used are those that would normally be considered waste, in which valuable psychoactive compounds are found only in lower concentrations. The mushroom parts may be ground using a milling machine or pulverization device, for example.

Ideally, the moisture content of the raw psychedelic organism after drying is low compared to the total dried biomass weight. For example, the moisture content may be under 5% for smaller scale extractions and under 10% for larger scale extractions. Wet mushrooms, e.g. with a moisture above 80%, will degrade rapidly. Dried biomass lends itself well to extraction since the drying process usually breaks down cell walls, allowing solvent to capture the molecules inside. The temperature of the oven and the drying time depend on how much moisture is in the raw psychedelic organism, and on the quantity of raw psychedelic organism.

The drying is carried out via vacuum desiccation, freeze drying, timed forced air drying or other drying method to obtain a dried biomass. For example, the drying is carried out in a forced air oven completely shielded from all light at 20-30° C. for a time period of 5-10 hours. However, there is room for optimization of the drying step, using different temperatures (e.g. 10-50° C.) and different durations, such as up to 48 hours. Besides the different quantities of biomass to be dried, the wide range of drying times corresponds to the wide range of available types of psychoactive organism. The aim is to dry the mushrooms so as not to significantly reduce their psychoactive alkaloid concentration. For example, if too high a temperature or too long a time at a specific temperature were used, the alkaloids may start to decompose. The dried biomass is ground, for example, to a mesh size of 100 or 200.

The solvent includes one or more liquids selected from a range of different liquids including lower aliphatic alcohols (C=1, 2, 3 or 4), C3-C4 ketones and water. The selected one or more liquids are acidified by the addition of an acid or by being buffered to an acidic pH. In some embodiments, the pH of the solvent is 56. The solvent, due to its acidity, promotes the dephosphorylation of any phosphorylated alkaloids present during the extraction process. Additionally, low pH extraction solvent will increase the ionic strength and polarity of the alkaloid by protonating the nitrogen moiety, increasing the solubility of the compound in polar solvents. If the pH is higher than 6, the nitrogen moiety will be deprotonated, and less soluble in polar solvents. For phosphorylated alkaloids, the yield may be lower when the pH is >6 due to the susceptibility of dephosphorylated alkaloids to oxidation, resulting in the formation of the quinoid dimer, which is inactive.

The acid may be acetic acid, adipic acid, ascorbic acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulphuric acid monobasic, calcium phosphate tribasic, citric acid, fumaric acid, gluconic acid, magnesium fumarate, malic acid, maleic acid, maleonic acid, oxalic acid, succinic acid, gluconic acid, glutamic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate or tartaric acid, and any combination selected from these. In some embodiments, the acid is either only hydrochloric acid or only phosphoric acid, for example. It is also envisaged that other acids may be used, for example non-food-grade acids that may be used by pharmaceuticals.

A wide range of solvent to solid ratios can be used. Typically, a 1 to 50:1 solvent-solid ratio (L:kg) may be used for the extraction. In one embodiment, the extraction is performed with a solvent to solid ratio of 20 L:1 kg. The amount of solvent used generally varies according to the weight of the biomass.

In extraction step 10, as a result of adding the solvent, and soaking the biomass in the solvent, essential elements or psychoactive alkaloids found in the biomass dissolve into the solvent. The solvent may be at a low or high temperature, and pressure may be applied to the solvent. In some embodiments, the solvent is at room temperature. The optimal temperature of extraction varies depending on the solvent type used for the process. However, the optimal temperature for extraction is in the range of 5-95° C. In other embodiments, the temperature for extraction is in the range of 50-75° C. The useful temperature range generally spans most of the liquid state of the solvent used, and upper and lower limits are determined by physical practicalities and limits of the available apparatus. Still, the temperature of the solvent may be outside of this range in other embodiments. The duration of the extraction is from 10 minutes to 12 hours, with or without agitation. In other embodiments, the extraction is performed for a time period ranging from 30-240 minutes. Optimum duration is determined by experimentation, and depends on the chosen solvent and the strength of agitation in the extraction vessel.

If pressure is applied it may be in the range of 50 kPa-100 MPa above atmospheric (7-15,000 psig). The lower limit of pressure is indicative of when a benefit is seen in the rate at which the psychoactive alkaloids dissolve in the solvent, since the increased pressure may increase the reaction kinetics of the dissolution of the psychoactive alkaloids into the solvent. The upper limit is determined by what is physically practical given the constraints of equipment to safely operate under high pressure. Nevertheless, other pressures may be used. Solvent composition, particle size of the biomass and the temperature of extraction will determine how much pressure needs to be applied.

The extraction results in an extraction slurry, which is formed of undissolved solids from the biomass, some of which may be insoluble, and solvent, which now carries dissolved extract. Some of the undissolved solids may be undesirable components.

In step 12, the extraction slurry is filtered, resulting in a residue 14 (i.e. the undissolved solids of the biomass, some of which may be insoluble) and filtrate 16. The filtering step may be carried out with the extraction slurry still hot if the extraction step was heated, or it may first be allowed to cool. The extraction 10 and filtration 12 steps may be repeated multiple times on the same residue 14, with a fresh batch of solvent, which may have the same composition as the first solvent or it may be a different solvent.

In step 18, the filtrate 16 is retained for further treatment, or if the extraction and filtration steps are repeated, the filtrates 16 are combined and retained, and may be referred to as a bulk filtrate, pooled filtrate or psychoactive filtrate.

In step 20, the filtrate 16 is brought to an alkaline pH. For example, if the psychedelic alkaloid source is a biomass of *Psilocybe cubensis* mushrooms, which include primarily psilocybin and psilocin as the psychoactive alkaloids, then the pH is brought to a value of 9±0.5 in order to convert the psilocin cation in the filtrate to its deprotonated form. If the pH is below this range, then the conversion of the cationic form of the psilocin to the deprotonated form will not be complete. If the pH is above this range, then the psilocin will start to degrade unnecessarily. The pH should be brought within the range of 9±2 in step 20 for other psychoactive alkaloids.

The pH of the filtrate is adjusted using any strong or weak organic or mineral base. The base may be ammonium bicarbonate, ammonium carbonate, ammonium hydroxide, calcium acetate, calcium carbonate, calcium chloride, calcium hydroxide, calcium lactate, calcium oxide, calcium phosphate dibasic, calcium phosphate monobasic, magnesium carbonate, potassium aluminum sulphate, potassium bicarbonate, potassium carbonate, potassium hydroxide, potassium lactate, potassium phosphate dibasic, potassium pyrophosphate tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic, sodium phosphate tribasic or any combination therefrom. In one embodiment, the base is solely sodium hydroxide, for example. Other bases may be used in other embodiments, for example non-food-grade bases that may be used by pharmaceuticals.

For a first liquid-liquid extraction, a water-immiscible solvent should be chosen so that it is also immiscible with any alcohols and ketones that are in the extraction solvent. In cases where the extraction solvent has one or more components that are miscible with the desired water-immiscible solvent, then these components are removed from the basified filtrate before the liquid-liquid extraction. In step 21, removal of these components may be achieved, for example, by drying the basified filtrate and then re-suspending the resulting residue in water to result in a reconstituted basified filtrate. In some embodiments, step 21 is not necessary.

In step 22, the first liquid-liquid extraction is performed on the basified filtrate resulting from the prior step 20, or the reconstituted basified filtrate from step 21. The general term "basified filtrate" as used hereinafter refers to either the basified filtrate from step 20 or the reconstituted basified filtrate from step 21 depending on whether step 21 is implemented. The basified filtrate is considered to be aqueous, because the extraction solvent included water or the base added to the filtrate included water. For the first liquid-liquid extraction, the liquid added to the basified filtrate is a water-immiscible solvent, which may include, but is not limited to, benzene, butanol, butyl acetate, carbon tetrachloride, chloroform, cyclohexane, 1,2-dichloroethane, dichloromethane, diisopropyl ether, ethyl acetate, diethyl ether, heptane, hexane, isooctane, methyl tert-butyl ether, methyl ethyl ketone, pentane, tetrahydrofuran, trichloroethylene, toluene, xylene or naphthalene, or any combination of two or more selected from this list.

The liquid-liquid extraction may be carried out in a separatory funnel, for example, in which the basified filtrate and the water-immiscible solvent are vigorously shaken. During the liquid-liquid extraction, the psychoactive alkaloids pass from the aqueous phase (i.e. basified filtrate, which may include some alcohol and ketone) to the organic phase (water-immiscible solvent). Some of the non-psychoactive, extracted components, such as sugars, carbohydrates, salts, or polyphenols in the basified filtrate do not pass into the organic phase, therefore a degree of purification is achieved at this step. However, lipids and other nitrogenous compounds move into the organic phase. After allowing the phases to settle into layers, and separating them, the aqueous layer may be subjected to an assay for determining its alkaloid content using, for example, Dragendorff's reagent or high-performance liquid chromatography (HPLC). If there is a significant amount of alkaloid still in the aqueous layer, then the liquid-liquid extraction may be repeated on the aqueous layer with a fresh volume of water-immiscible solvent. Depending on the embodiment, the liquid-liquid extraction may be repeated 1-10 times, for example. If the liquid-liquid extraction is repeated, all the organic layers are combined after being separated from their respective aqueous layers. In step 24, the resulting organic layer, in which the psychoactive alkaloids are now dissolved, is retained for further treatment.

In step 26, a second liquid-liquid extraction is performed on the organic layer resulting from the prior step 24. For the second liquid-liquid extraction, the liquid added to the organic layer is weakly acidified water with an equivalent concentration of 0.001-0.5 N. The acid used to acidify the water may include, but is not limited to, acetic acid, adipic acid, ascorbic acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulphuric acid monobasic, calcium phosphate tribasic, citric acid, fumaric acid, gluconic acid, magnesium fumarate, malic acid, maleic acid, maleonic acid, oxalic acid, succinic acid, gluconic acid, glutamic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate or tartaric acid, or any combination of two or more selected from this list.

The second liquid-liquid extraction may also be carried out in a separatory funnel, for example, in which the retained organic layer and the weakly acidified water are vigorously shaken. During the liquid-liquid extraction, the psychoactive alkaloids pass from the organic phase to the aqueous phase (weakly-acidified water). Some of the non-psychoactive, extracted components, such as lipids, tocopherols, fatty acids, proteins or other nitrogenous compounds in the organic phase do not pass into the aqueous phase, therefore another degree of purification is achieved at this step. However, other nitrogenous or similarly ionizable compounds (any compound that can achieve both ionic polarizability and neutrality in a similar way that an alkaloid can) may pass into the aqueous phase, for example: urea or uric acid, some proteins, tyrosine, tryptophan and ergosterol. After allowing the layers to settle, and separating them, the organic layer may be subjected to an assay for determining its alkaloid content using, for example, Dragendorff's reagent or high-performance liquid chromatography (HPLC). If there is a significant amount of alkaloid still in the organic layer, then the second liquid-liquid extraction may be repeated on the organic layer with a fresh volume of weakly acidified water. Depending on the embodiment, the second liquid-liquid extraction may be repeated 1-5 times, for example. If the liquid-liquid extraction is repeated, all the aqueous layers are combined after being separated from their respective organic layers. In step 28, the resulting aqueous layer, in which the psychoactive alkaloids are now dissolved, is retained for further treatment.

In step 30, evaporation of the water results in a powdered extract. Evaporation of the water may make use of a rotary evaporator followed by freeze-drying. In other embodiments, other drying techniques may be employed. The resulting psychoactive alkaloid composition may be in a free-flowing powder form, which allows for the composition to be easily handled. Other compounds may be included in the extract. These may be proteins, carbohydrates, fats, and nitrogenous compounds such as urea, uric acid, ergosterols, or amino acids, and may make up about 10% of the extract.

If the evaporation of the water is not interrupted for standardization, then standardization occurs at step 32. In the standardization step 32, the concentration of psychoactive alkaloids in the extract is measured. HPLC coupled with diode array detection or mass spectrometry is used to determine the alkaloid content of the dried powder extract. In some embodiments, additional characterization techniques such thermal analysis, particle size analysis, X-ray diffraction, etc. may be run to identify the physical properties of the dried powder extract. A suitable quantity of excipient is added to the extract to result in a composition with a specified concentration of dephosphorylated psychoactive alkaloids, thereby achieving standardization of the extract. The excipient added in the standardization process may include a stabilizer, a carrier, or any other type of excipient depending on the desired properties of the formulation.

The standardized, dried powdered extract, or formulation, has a known concentration by weight of psychoactive compound(s). The particular psychoactive alkaloids that are present in the standardized extract may be determined by HPLC. The standardized extract is a powdered extract that may have, for example, a total dephosphorylated psychoactive alkaloid concentration, when expressed in a conjugate salt form, of 0.1-99% by dry weight. In other embodiments, for example where the psychedelic organism includes psychoactive alkaloids that are not phosphorylatable, which are extracted alongside the dephosphorylated alkaloids, then the dried powder extract may have a total psychoactive alkaloid salt concentration of 0.1-99% by dry weight. The resulting composition can be of pharmaceutical, nutraceutical, or veterinarian grade.

If the evaporation of the water in step 30 is interrupted for standardization, then the slurry or liquid that has been partially concentrated due to the evaporation is analyzed for dry mass content and total psychoactive alkaloid content. This entails analyzing a small sample of the slurry or liquid. Based on the dry mass content and the psychoactive alkaloid content, then an amount of excipient can be calculated, such that when added to the slurry or liquid, results in a desired psychoactive concentration (wt/wt %) in the psychoactive composition when the evaporation is complete.

In some embodiments, it is possible to use a neutral solvent at step 10, i.e. without the addition of the acid. In this case the extracted psychoactive alkaloid may be partially dephosphorylated and partially phosphorylated.

C. Process Starting from Extract

Figure 2:
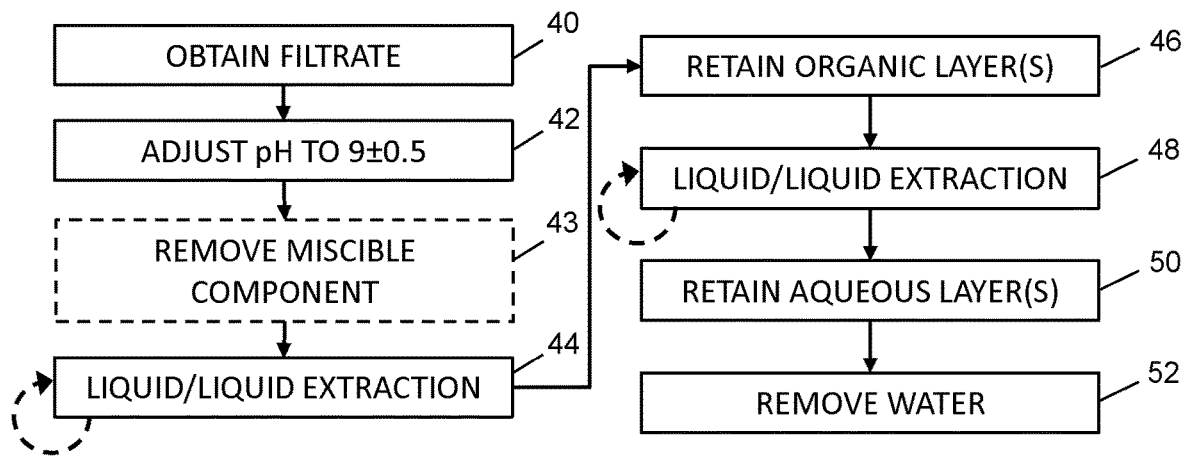
FIG. 2 is a flowchart showing a process for extracting psychoactive alkaloids from a pre-existing extract, according to an embodiment of the present invention.
Figure 3:
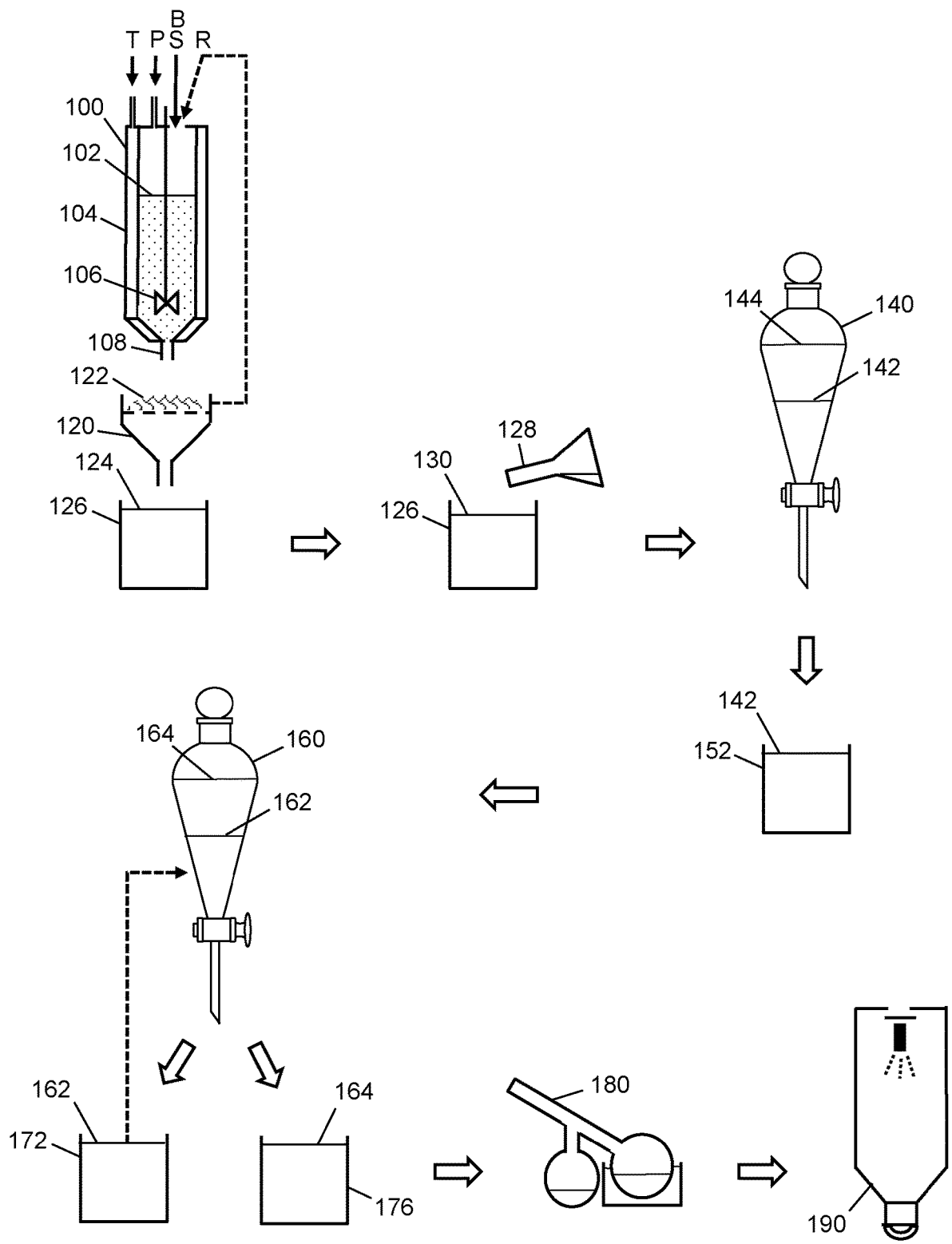
FIG. 3 is a schematic diagram of the apparatus used for the extraction of psychoactive compounds, according to embodiments of the present invention.

FIG. 2 outlines a process where the psychoactive alkaloid source is a pre-existing extract, which in general will have a lower psychoactive alkaloid content compared to the psychoactive alkaloid content in the final extract after going through the extraction process described herein.

In step 40, a psychoactive filtrate is obtained from the psychoactive alkaloid source using a solvent which is, or includes, a C1-C4 aliphatic alcohol, a C3-C4 ketone, water, or any combination selected from these. As for the extraction from raw biomass, the solvent is acidified by the addition of an acid or by being buffered to an acidic pH. In some embodiments, the pH of the solvent is 56, and in other embodiments, the pH is 54. Obtaining the filtrate may involve soaking the pre-existing extract in the solvent and agitating the mixture of the extract and the solvent. The temperature of the soaking step may be in the range 5-95° C., and the duration of the soaking may be, for example, 10 minutes to 12 hours. After soaking, a filtration step follows to produce the psychoactive filtrate.

In step 42, the filtrate is brought to an alkaline pH. For example, if the psychedelic alkaloid source is an extract of *Psilocybe cubensis* mushrooms, which include primarily psilocybin and psilocin as the psychoactive alkaloids, then the pH is brought to a value of 9±0.5 in order to convert the psilocin cation in the filtrate to its deprotonated form. The pH should be brought within the range of 9±2 in step 20 for other psychoactive alkaloids. After step 42, the filtrate can be considered to be a basified psychoactive filtrate.

In step 43, if necessary, then components in the solvent that are miscible with the water-immiscible solvent for the first liquid-liquid extraction are removed. This results in a reconstituted basified filtrate that is immiscible with the water-immiscible solvent.

In step 44, a first liquid-liquid extraction is performed, in a similar way to step 22 of FIG. 1. The organic phase is retained in step 46 and a second liquid-liquid extraction is performed on it in step 48, in a similar way to step 26 of FIG. 1. The aqueous phase is retained in step 50 and then dried in step 52. The evaporation of the water in step 50 may be interrupted to standardize the extract, or standardization may be carried out after the drying.

The result is a dry, psychoactive extract with a psychoactive alkaloid concentration, by weight, that is higher than the concentration of the psychoactive alkaloid in the pre-existing extract. Due to the liquid-liquid extractions, some of the undesired components present in the pre-existing extract are removed, leading to a resulting extract of higher purity than the pre-existing extract.

In some embodiments, it is possible to use a neutral solvent to obtain the filtrate, i.e. without the addition of the acid to the solvent for step 40. In this case the extracted psychoactive alkaloid may not be fully dephosphorylated.

D. Example

A mass of 10 kg of raw psychedelic mushrooms from the *Psilocybe cubensis* species was dried in a forced air oven at 25° C. for 7.5 hours. The resulting, dried biomass was 489.3 g, which was pulverized to a particle size of 100 mesh using a cutting mill.

The dried powdered biomass was placed into an agitated, heat-controlled vessel with 10 liters of solvent. In this embodiment, the solvent was 2.5 M acetic acid in water. The extraction was controlled to a constant 70° C., and the duration of extraction was 45 minutes. After extraction, the resulting extraction slurry was filtered while hot, and the filter residue was placed back into the extraction vessel and extracted with an additional 10 liters of 2.5 M acetic acid. The temperature of extraction was again 70° C. and the duration of extraction was 45 minutes. The extraction slurry was again filtered while hot and the filtrates from the first and second extraction were pooled to form a bulk filtrate.

The bulk filtrate was placed into an agitated separation vessel and the pH was titrated to pH 8.95 with 5 M sodium carbonate. The water-immiscible solvent used for the first liquid-liquid extraction was a volume of 1 L of chloroform, which was then added to the separation vessel. The mixture in the separation vessel was agitated for 10 minutes before being allowed to separate. The bottom, organic layer was removed and retained. Again, 1 L of chloroform was added to the aqueous layer remaining in the separation vessel, the mixture agitated and allowed to separate, and the bottom, organic layer removed and retained. The process was repeated three times before pooling the organic layers together to form 4 L of chloroform extract (a "psychoactive organic layer").

The chloroform extract was then placed into a new separation vessel along with a 500 mL solution of 0.10% fumaric acid in water (weakly acidified water). This separation vessel was agitated for 15 minutes before the layers were allowed to settle and then separated. The upper, aqueous layer was set aside. An additional 500 mL of 0.10% fumaric acid in water was combined with the chloroform extract in the separation vessel. The total volume and strength chosen for the weakly acidified water depend on the estimated amount of alkaloid and the desire to have a small excess of fumarate (e.g. 5%). If there is too much fumarate, then the purity of the extract may be decreased. The separation vessel was again agitated for 15 minutes before allowing separation of the mixture inside. The layers were removed and the two aqueous layers were combined to make 1000 mL of liquid, purified psychoactive alkaloid extract (a "psychoactive aqueous layer"). The psychoactive aqueous layer was concentrated using a rotary evaporator to 100 mL and then subjected to lyophilization to make 2.34 g of a dry purified psychoactive alkaloid extract containing 1.69 g of psilocin. The concentration of psilocin was therefore 72.24 dry wt/wt %. The concentration of psilocin, expressed as the fumarate salt $(C_{12}H_{16}N_2O)_2+(C_4H_4O_4)$, was therefore 91.33 dry wt/wt %.

E. Apparatus

Referring to FIG. 2, an example of the apparatus is shown schematically. A biomass (B) of raw, dried and pulverized psychedelic organisms, such as psilocybin mushrooms is placed in an agitated, heat-controlled extraction vessel 100. Alternately, a pre-existing extract may be used. The solvent (S), such as a neutral or acidified C1-C4 aliphatic alcohol, a neutral or acidified C3-C4 ketone, water, acidified water, buffered acid, or any mixture of any selection therefrom, is also placed into the extraction vessel 100. The vessel may be surrounded by an insulating wall 104 that helps to maintain the contents 102, i.e. the biomass and solvent, at a steady temperature (T). Alternately, there may be an insulating jacket wrapped around the vessel. The insulating wall 104 or jacket helps to maintain the contents 102 under a constant temperature between 5-95° C. The pressure (P) inside the extraction vessel 100 may be regulated up to 100 MPa (15,000 psig). A stirrer 106 or other agitation device is used to mix the contents of the extraction vessel, either continuously or periodically.

After the extraction, the bottom of the extraction vessel 100 is opened at outlet 108 and the extraction slurry is then fed into filter 120. The filter 120 separates the residue 122 from the filtrate 124, which passes through the filter 120 and is collected in container 126. The residue 122 is then fed back, if required, at R into the agitated, heat-controlled extraction vessel 100 and more solvent (S) is added. After the second or any other subsequent extraction, the extraction slurry is released from the extraction vessel 100 and fed into filter 120 or another filter. After each filtration, the filtrate is collected in container 126.

After the one, two or more filtration stages, a base is added from flask 128 as necessary to the filtrate in container 126, to result in the basified filtrate 130. The basified filtrate 130 is then transferred to a separatory funnel 140, as is a water-immiscible solvent.

The basified filtrate and the water-immiscible solvent are then vigorously mixed, e.g. by shaking the separatory funnel 140. After mixing, and after allowing the mixture to separate, a bottom, organic layer 142 and a top, aqueous layer 144 are formed. The bottom organic layer 142, which now includes extracted psychoactive alkaloids, is drawn off into container 152. If the first liquid-liquid extraction is repeated, the organic layers are combined in container 152.

The second liquid-liquid extraction is performed using separatory funnel 160, into which the organic layer 142 from the prior liquid-liquid extraction and weakly acidified water are placed. The prior organic layer and weakly acidic water are then vigorously mixed, e.g. by shaking the separatory funnel. After mixing, and after allowing the mixture to separate, a new bottom organic layer 162 and a new top aqueous layer 164 are formed. The bottom organic layer 162, which now has reduced extracted psychoactive alkaloids, is drawn off into container 172. The top, aqueous layer 164, which now includes extracted psychoactive alkaloids, is drawn off into container 176. If the second liquid-liquid extraction is repeated, then the bottom organic layer 162 is returned to the separatory funnel 160 with a fresh volume of weakly acidified water, and after the extraction the resulting aqueous layer is added to the aqueous phase 164 in container 176.

The aqueous phase 164, in which the psychoactive alkaloids are dissolved, is then concentrated in a rotary evaporator 180. The resulting concentrate is then dried in a freeze dryer 190 to result in a powdered, purified psychoactive extract.

F. Variations

In other embodiments, other drying techniques, temperatures and durations may be used. It is possible in other embodiments to grind the dried biomass to lower or higher particle size than 100 or 200 mesh. For example, grinding to a mesh size of 40 would work in some embodiments. The choice of solvent may have an impact on which mesh size to grind the dried mushrooms or other organisms to. The grinding step may take place before or after the drying step. The extraction process in other embodiments may use varying applied pressures and temperatures, which vary during the soaking steps.

The water used may be purified. For example, it may be reverse osmosis water.

Any of the solvents described herein may be used with any of the organisms that have psychoactive alkaloids.

The process may be scaled up using larger quantities and modified apparatus.

Temperatures that have been given to the nearest degree include all temperatures within a range of ±0.5° C. of the given value. Likewise, numbers and percentages are specified to the nearest significant digit. Values of pH are specified to ±0.5.

All ranges given include all subranges within the range. For example, if a range is given as m-q, then the ranges m-n, n-p and p-q are included, where n and p are any values that satisfy m<n<p<q.

Other embodiments are also possible. Embodiments, depending on their configuration, may exhibit all or fewer than all of the advantages described herein.

In general, unless otherwise indicated, singular elements may be in the plural and vice versa with no loss of generality.

The words "organism", "alkaloid" and "excipient" are used both as countable nouns and uncountable nouns.

Throughout the description, specific details have been set forth in order to provide a more thorough understanding of the invention. However, the invention may be practised without these particulars. In other instances, well known elements have not been shown or described in detail and repetitions of steps and features have been omitted to avoid unnecessarily obscuring the invention. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. Steps in the flowchart may be removed or other steps added without altering the main outcome of the process.

All parameters, dimensions, materials, quantities and configurations described herein are examples only and may be changed depending on the specific embodiment. Accordingly, the scope of the invention is to be construed in accordance with the substance defined by the following claims.

The invention claimed is:

1. A process for forming a dry, psychoactive extract comprising a salt of a psychoactive alkaloid in its dephophorylated form from a biomass of one or more dried, ground, raw psychedelic organisms comprising *Amanita muscaria, Psilocybe cubensis*, Psilocybe cyanescens, or any combination selected therefrom, the process comprising the steps of:
    obtaining a psychoactive filtrate from the biomass using a solvent consisting of an acid and one or more members selected from the group consisting of C1-C4 aliphatic alcohols, C3-C4 ketones and water, wherein the psychoactive filtrate comprises the psychoactive alkaloid in its dephosphorylated form, which comprises psilocin, norpsilocin, 4-hydroxytryptamine, N, N, N-trimethyl-4-hydroxytryptamine or any combination selected therefrom;
    basifying the psychoactive filtrate to result in a basified psychoactive filtrate;
    performing a first liquid-liquid extraction on the basified psychoactive filtrate using a water-immiscible solvent to yield a psychoactive organic layer, wherein the water-immiscible solvent is immiscible with the basified psychoactive filtrate;
    performing a second liquid-liquid extraction on the psychoactive organic layer using weakly-acidified water to yield a psychoactive aqueous layer, wherein the weakly-acidified water has a concentration in a range of 0.001-0.5 N; and
    removing water from the psychoactive aqueous layer to yield the dry, psychoactive extract comprising the salt of the psychoactive alkaloid in its dephosphorylated form.

2. The process of claim 1, comprising removing one or more components of the solvent from the basified psychoactive filtrate before the first liquid-liquid extraction, wherein the one or more components are miscible with the water-immiscible solvent.

3. The process of claim 1, wherein the obtaining step comprises:
    soaking the biomass in the solvent; and
    filtering an undissolved portion of the biomass from the solvent to result in the psychoactive filtrate.

4. The process of claim 3, wherein the soaking step is at a temperature of 5-95° C.

5. The process of claim 3, comprising applying a pressure of 50 kPa-100 MPa to the solvent during the soaking step.

6. The process of claim 3, comprising agitating the solvent during the soaking step, wherein the soaking step has a duration of 10 minutes to 12 hours.

7. The process of claim 3 comprising:
    repeating, using further solvent, the soaking and filtering steps for the undissolved portion of the biomass to result in a further psychoactive filtrate, and
    combining the psychoactive filtrate, after the filtering step, with the further psychoactive filtrate.

8. The process of claim 1, wherein the solvent has a pH≤6.

9. The process of claim 8, wherein the solvent has a pH≤4.

10. The process of claim 1, wherein the acid is acetic acid, adipic acid, ascorbic acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulphuric acid monobasic, calcium phosphate tribasic, citric acid, fumaric acid, gluconic acid, magnesium fumarate, malic acid, maleic acid, maleonic acid, oxalic acid, succinic acid, gluconic acid, glutamic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate or tartaric acid, or any combination selected therefrom.

11. The process of claim 1, wherein a ratio of the solvent to the biomass is in a range from 1L:1 kg to 50L:1 kg.

12. The process of claim 1, wherein the salt is a fumarate salt.

13. The process of claim 1, wherein the basified psychoactive filtrate has a pH=9±0.5.

14. The process of claim 1, wherein the basified psychoactive filtrate has a pH=9±2.

15. The process of claim 1, wherein the psychoactive filtrate is basified by adding ammonium bicarbonate, ammonium carbonate, ammonium hydroxide, calcium acetate, calcium carbonate, calcium chloride, calcium hydroxide, calcium lactate, calcium oxide, calcium phosphate dibasic, calcium phosphate monobasic, magnesium carbonate, potassium aluminum sulphate, potassium bicarbonate, potassium carbonate, potassium hydroxide, potassium lactate, potassium phosphate dibasic, potassium pyrophosphate tetrabasic, potassium phosphate tribasic, potassium tripolyphosphate, sodium acetate, sodium acid pyrophosphate, sodium aluminum phosphate, sodium aluminum sulphate, sodium bicarbonate, sodium bisulphate, sodium carbonate, sodium hexametaphosphate, sodium hydroxide, sodium lactate, sodium phosphate dibasic, sodium phosphate monobasic or sodium phosphate tribasic, or any combination selected therefrom.

16. The process of claim 1, wherein the water-immiscible solvent is benzene, butanol, butyl acetate, carbon tetrachloride, chloroform, cyclohexane, 1,2-dichloroethane, dichloromethane, diisopropyl ether, ethyl acetate, diethyl ether, heptane, hexane, isooctane, methyl tert-butyl ether, methyl ethyl ketone, pentane, tetrahydrofuran, trichloroethylene, toluene, xylene or naphthalene, or any combination selected therefrom.

17. The process of claim 1, comprising forming the weakly-acidified water using acetic acid, adipic acid, ascorbic acid, ammonium aluminum sulphate, ammonium citrate dibasic, ammonium citrate monobasic, calcium citrate, calcium fumarate, calcium gluconate, calcium phosphate dibasic, calcium phosphate monobasic, hydrochloric acid, sulphuric acid monobasic, calcium phosphate tribasic, citric acid, fumaric acid, gluconic acid, magnesium fumarate, malic acid, maleic acid, maleonic acid, oxalic acid, succinic acid, gluconic acid, glutamic acid, phosphoric acid, potassium acid tartrate, potassium citrate, potassium fumarate, sodium citrate, sodium fumarate, sodium gluconate, sodium lactate, sodium potassium hexametaphosphate, sodium potassium tartrate, sodium potassium tripolyphosphate, sodium pyrophosphate tetrabasic, sodium tripolyphosphate or tartaric acid, or any combination selected therefrom.

18. The process of claim 1, wherein removing the water comprises evaporating a portion of the water with a rotary evaporator and a remainder of the water by freeze-drying.

19. The process of claim 1 comprising, before the second liquid-liquid extraction:
  repeating, using further water-immiscible solvent, the first liquid-liquid extraction on the basified psychoactive filtrate to yield a further psychoactive organic layer; and
  adding the further psychoactive organic layer to the psychoactive organic layer.

20. The process of claim 1 comprising, before removing the water:
  repeating, using further weakly-acidified water, the second liquid-liquid extraction on the psychoactive organic layer to yield a further psychoactive aqueous layer; and
  adding the further psychoactive aqueous layer to the psychoactive aqueous layer.

* * * * *